(12) United States Patent
Shiki

(10) Patent No.: US 11,123,045 B2
(45) Date of Patent: Sep. 21, 2021

(54) ULTRASONIC DIAGNOSTIC APPARATUS AND MEDICAL IMAGE PROCESSING APPARATUS

(71) Applicant: TOSHIBA MEDICAL SYSTEMS CORPORATION, Otawara (JP)

(72) Inventor: Eiichi Shiki, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 249 days.

(21) Appl. No.: 15/439,427

(22) Filed: Feb. 22, 2017

(65) Prior Publication Data

US 2017/0340312 A1    Nov. 30, 2017

(30) Foreign Application Priority Data

May 26, 2016  (JP) .............................. JP2016-105402
Feb. 14, 2017  (JP) ................................. 2017-025041

(51) Int. Cl.
*A61B 8/08* (2006.01)
*A61B 8/00* (2006.01)
(Continued)

(52) U.S. Cl.
CPC .......... *A61B 8/5215* (2013.01); *A61B 8/4254* (2013.01); *A61B 8/4444* (2013.01);
(Continued)

(58) Field of Classification Search
CPC ..... A61B 8/4254; A61B 8/4444; A61B 8/466; A61B 8/483; A61B 8/5207; A61B 8/5215;
(Continued)

(56) References Cited

U.S. PATENT DOCUMENTS 5,787,889 A * 8/1998 Edwards ............. G01S 15/8993
128/916
6,014,473 A * 1/2000 Hossack ................ A61B 8/145
348/169
(Continued)

FOREIGN PATENT DOCUMENTS

JP            8-332187        12/1996
JP       2000-157541 A        6/2000
(Continued)

OTHER PUBLICATIONS

K. L. Watkin, et al., "Three-dimensional Reconstruction and Enhancement of Arbitrarily Oriented and Positioned 2D Medical Ultrasonic Images," CCECE/CCGEI '93, 1993 IEEE, 1188-1195. (Year: 1993).*
(Continued)

*Primary Examiner* — Joanne M Hoffman
*Assistant Examiner* — Alexei Bykhovski
(74) *Attorney, Agent, or Firm* — Oblon, McClelland, Maier & Neustadt, L.L.P.

(57) ABSTRACT

An ultrasonic diagnostic apparatus according to a present embodiment includes: a transmitting and receiving circuit configured to transmit an ultrasonic wave to an ultrasonic probe and receive a signal based on the ultrasonic wave received by the ultrasonic probe; a generation circuit configured to generate multiple 2D image data in a chronological order based on the signal; an acquisition circuit configured to acquire multiple positional data of the ultrasonic probe; a memory circuit; a processing circuit configured to perform processing in such a manner that the multiple 2D image data arranged in the memory circuit according to the multiple positional data fit inside a memory space of the
(Continued)

memory circuit; and a volume generation circuit configured to generate volume data in the memory space based on the processed multiple 2D image data.

15 Claims, 15 Drawing Sheets

(51) Int. Cl.
  *G06T 7/00*   (2017.01)
  *G01S 7/52*   (2006.01)
  *G01S 15/89*  (2006.01)

(52) U.S. Cl.
  CPC .............. *A61B 8/466* (2013.01); *A61B 8/483* (2013.01); *A61B 8/5207* (2013.01); *G01S 7/52034* (2013.01); *G01S 7/52068* (2013.01); *G01S 7/52085* (2013.01); *G01S 15/8993* (2013.01)

(58) Field of Classification Search
  CPC .............. G01S 15/8993; G01S 7/52034; G01S 7/52068; G01S 7/52085
  See application file for complete search history.

(56) References Cited

U.S. PATENT DOCUMENTS

| | | | | |
|---|---|---|---|---|
| 7,609,884 | B1 * | 10/2009 | Stalling | G06K 9/6212 |
| | | | | 382/168 |
| 8,645,294 | B1 * | 2/2014 | Owechko | G06N 5/043 |
| | | | | 706/14 |
| 2008/0095465 | A1 * | 4/2008 | Mullick | G06K 9/6206 |
| | | | | 382/284 |
| 2012/0027282 | A1 * | 2/2012 | Yoshikawa | A61B 8/13 |
| | | | | 382/131 |
| 2015/0297193 | A1 * | 10/2015 | Rothberg | A61B 8/4483 |
| | | | | 600/459 |

FOREIGN PATENT DOCUMENTS

| | | | | |
|---|---|---|---|---|
| JP | 2008-125692 A | * | 11/2006 | .............. A61B 8/145 |
| JP | 5296975 B2 | * | 11/2006 | .............. A61B 8/145 |
| JP | 2008-125692 A | | 6/2008 | |
| JP | 4493316 | | 6/2010 | |

OTHER PUBLICATIONS

Japanese Office Action dated Nov. 10, 2020 in Japanese Patent Application No. 2017-025041, 4 pages.

* cited by examiner

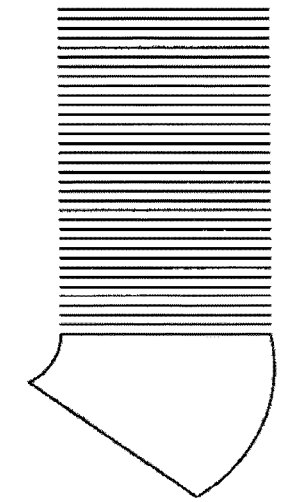
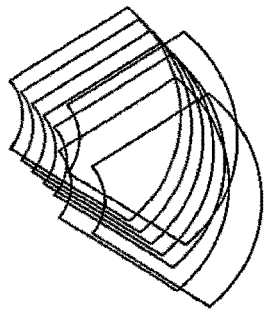
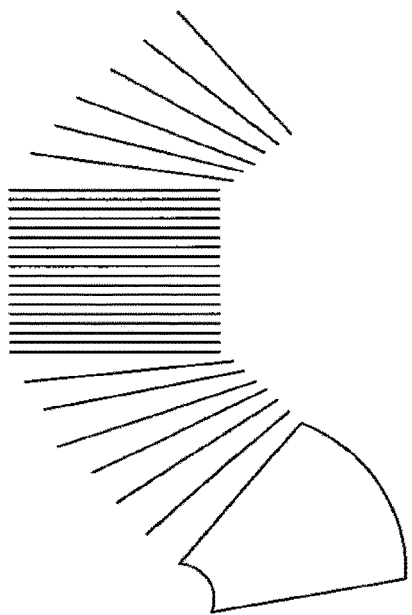
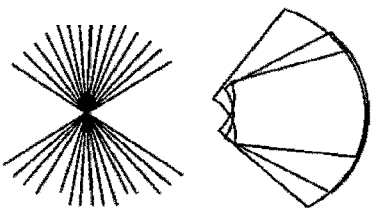
FIG. 5A LINEAR SWEEP
FIG. 5B SECTOR SWEEP
FIG. 5C PUSHING ASIDE, SIDESPIN AND S-SWEEPS
FIG. 5D COMPOUND SWEEP
FIG. 5E ROTATION SWEEP (TOP VIEW)

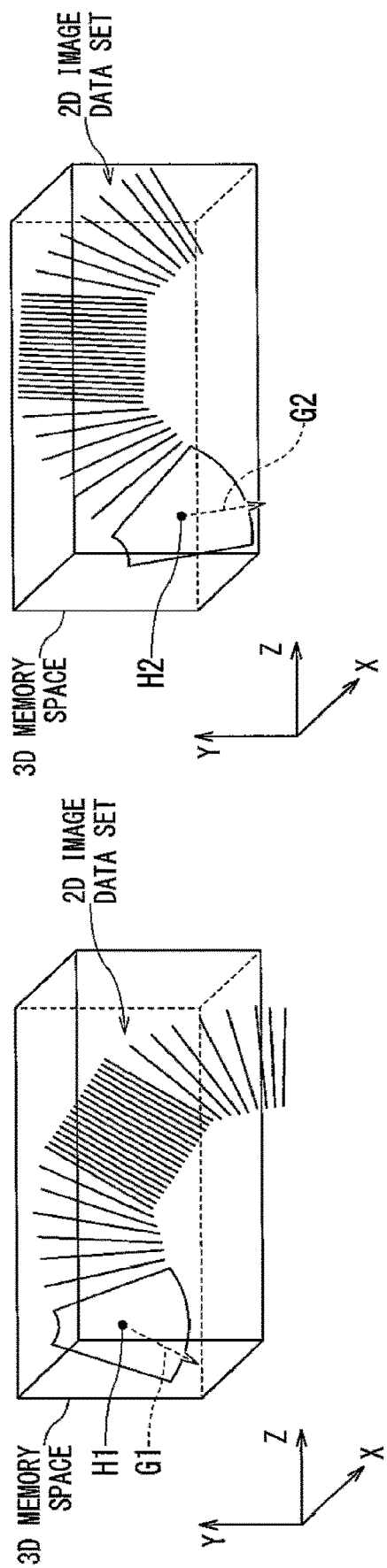

ULTRASONIC DIAGNOSTIC APPARATUS AND MEDICAL IMAGE PROCESSING APPARATUS

CROSS-REFERENCE TO RELATED APPLICATION

This application is based upon and claims the benefit of priority from Japanese Patent Application No. 2016-105402, filed on May 26, 2016, and Japanese Patent Application No. 2017-25041, filed on Feb. 14, 2017, the entire contents of each of which are incorporated herein by reference.

FIELD

An embodiment as an aspect of the present invention relates to an ultrasonic diagnostic apparatus and a medical image processing apparatus.

BACKGROUND

In the medical field, an ultrasonic diagnostic apparatus is used for imaging the inside of a subject using ultrasonic waves generated by multiple transducers (piezoelectric transducers) of an ultrasonic probe. The ultrasonic diagnostic apparatus causes the ultrasonic probe, which is connected to the ultrasonic diagnostic apparatus, to transmit ultrasonic waves into the subject, generates a received signal based on a reflected wave, and obtains a desired ultrasonic image by image processing.

An operator may acquire multiple 2D image data in a chronological order while moving the ultrasonic probe, and may also acquire multiple positional data of the ultrasonic probe. In this case, the ultrasonic diagnostic apparatus arranges the multiple 2D image data based on the respective multiple positional data and three-dimensionally reconstructs the image data, to thereby generate and display 3D image data.

A problem to be solved by the invention is to provide an ultrasonic diagnostic apparatus and a medical image processing apparatus which are capable of improving diagnostic capabilities using a 3D image to be displayed based on the multiple 2D image data.

BRIEF DESCRIPTION OF THE DRAWINGS

In accompanying drawings,

FIGS. 5A to 5E are diagrams showing types of sweep formats used by the ultrasonic probe;

FIGS. 9A and 9B are conceptual diagrams showing an orientation change processing performed by the processing circuit;

DETAILED DESCRIPTION

An ultrasonic diagnostic apparatus and a medical image processing apparatus according to a present embodiment will be described with reference to the accompanying drawings.

The ultrasonic diagnostic apparatus according to the present embodiment includes: a transmitting and receiving circuit configured to transmit an ultrasonic wave to an ultrasonic probe and receive a signal based on the ultrasonic wave received by the ultrasonic probe; a generation circuit configured to generate multiple 2D image data in a chronological order based on the signal; an acquisition circuit configured to acquire multiple positional data of the ultrasonic probe; a memory circuit; a processing circuit configured to perform processing in such a manner that the multiple 2D image data arranged in the memory circuit according to the multiple positional data fit inside a memory space of the memory circuit; and a volume generation circuit configured to generate volume data in the memory space based on the processed multiple 2D image data.

1. Ultrasonic Diagnostic Apparatus According to a Present Embodiment

Figure 1:
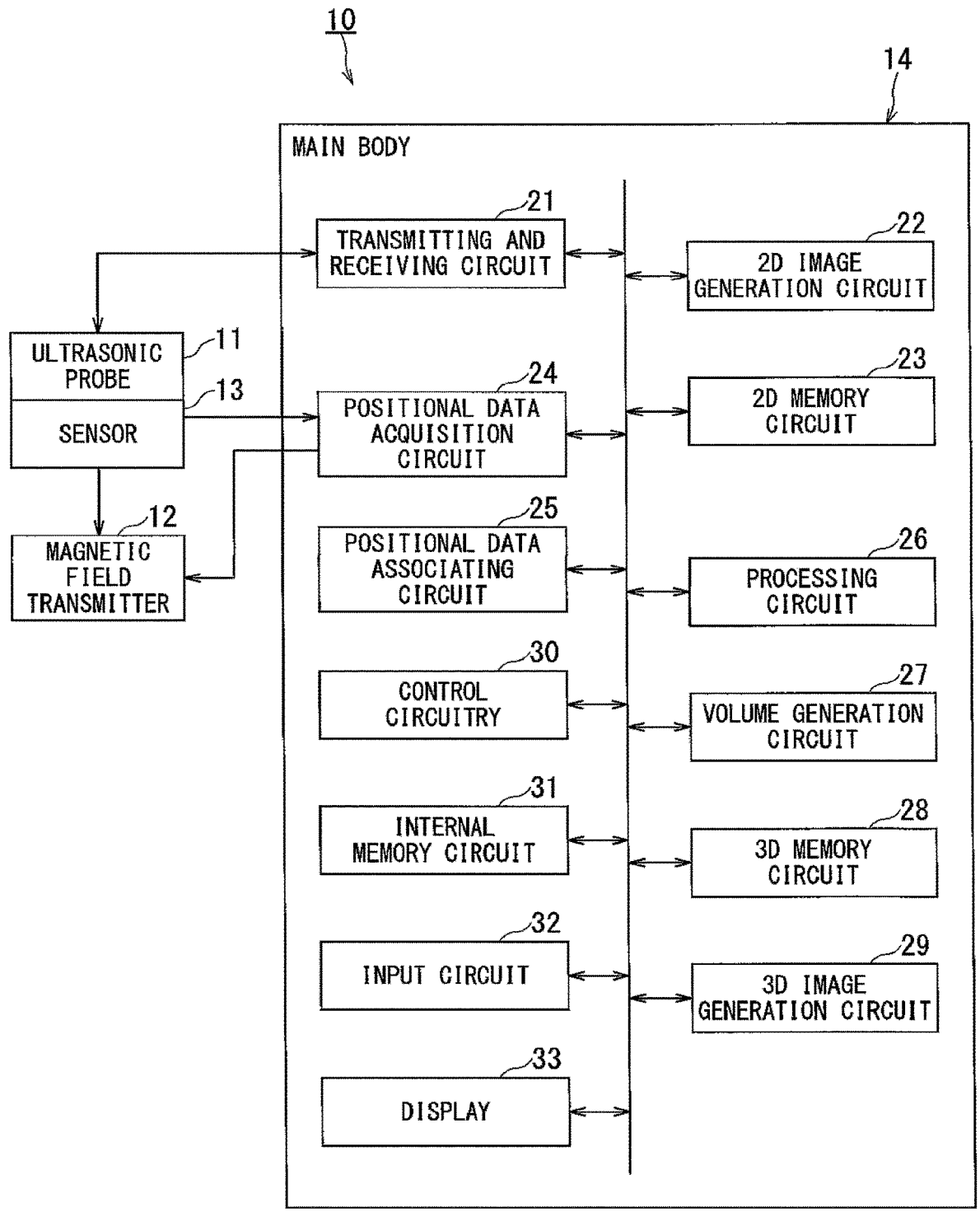
FIG. 1 is a schematic diagram showing a configuration of an ultrasonic diagnostic apparatus according to a present embodiment.

FIG. 1 is a schematic diagram showing a configuration of an ultrasonic diagnostic apparatus according to a present embodiment.

FIG. 1 shows an ultrasonic diagnostic apparatus 10 according to the present embodiment. The ultrasonic diagnostic apparatus 10 includes an ultrasonic probe 11, a magnetic field transmitter 12, a sensor 13, and a main body 14. Note that only the main body 14 may be referred to as the ultrasonic diagnostic apparatus. In this case, the ultrasonic diagnostic apparatus is connected to the ultrasonic probe, the magnetic field transmitter, and the sensor which are provided outside of the ultrasonic diagnostic apparatus.

The ultrasonic probe 11 transmits an ultrasonic wave to a subject (for example, a patient) or receives an ultrasonic wave from the subject. The ultrasonic probe 11 brings the front surface thereof into contact with the surface of the subject to transmit an ultrasonic wave to the subject or receive an ultrasonic wave from the subject. The ultrasonic probe 11 includes small transducers (piezoelectric elements) that are one-dimensionally (1D) or two-dimensionally (2D) arranged at a tip end of the ultrasonic probe. Each of the transducers is an electroacoustic conversion element and has a function of converting an electric pulse into an ultrasonic pulse during transmission and converting a reflected wave into an electric signal (received signal) during reception.

The ultrasonic probe 11 is formed to have a small size and a light weight, and is connected to the main body 14 through a cable. Examples of the type of the ultrasonic probe 11 include a 1D array probe, a mechanical 4D probe, and a 2D array probe. The 1D array probe has a configuration in which transducers are one-dimensionally arranged. In this case, the 1D array probe also includes a configuration in which a small number of transducers are arranged in an elevation direction.

Figure 2:
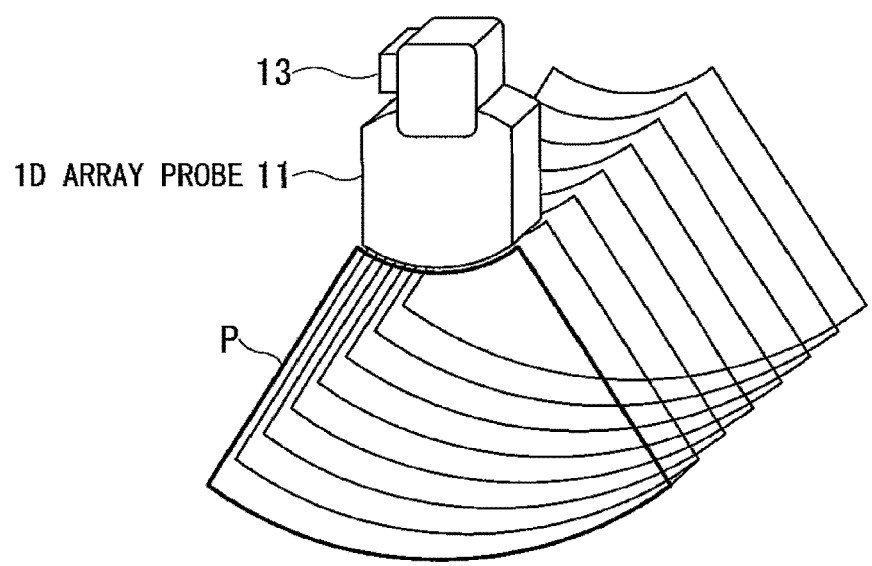
FIG. 2 is a diagram for explaining scanning surfaces of an ultrasonic probe.

FIG. 2 is a diagram for explaining scanning surfaces of the ultrasonic probe 11.

FIG. 2 shows a movement of a scanning surface P when the operator manipulates and moves the 1D array probe as the ultrasonic probe 11. In this case, the positions of the sensor 13 and the scanning surface P are both fixed with respect to the 1D array probe 11. Accordingly, the conversion of a geometric positional relationship from the sensor 13 to the scanning surface P makes it possible to obtain positional data of the scanning surface P from the positional data of the sensor 13. The operator moves the 1D array probe 11 in a direction intersecting with the scanning surface P, thereby performing a so-called three-dimensional scanning. Examples of the movement of the 1D array probe 11 include a parallel movement, tilting, and rotation, and the same applies in the following description.

Referring again to FIG. 1, the magnetic field transmitter 12 is disposed in the vicinity of the ultrasonic probe 11 so that the sensor 13 fits inside an effective range of a magnetic field generated from the magnetic field transmitter 12. The magnetic field transmitter 12 generates the magnetic field by the control of the main body 14.

The sensor 13 detects multiple positional data of the ultrasonic probe 11 in a chronological order and outputs the multiple positional data to the main body 14. The sensor 13 is divided into two types, i.e., a sensor that is attached to the ultrasonic probe 11 and a sensor that is provided separately from the ultrasonic probe 11. The latter type is an optical sensor which photographs feature points of the ultrasonic probe 11 to be measured from multiple positions, and detects each position of the ultrasonic probe 11 according to the principle of triangulation. A case where the former type is used as the sensor 13 will be described below.

The sensor 13 is attached to the ultrasonic probe 11, detects the positional data of the sensor 13 itself, and outputs the detected positional data to the main body 14. The positional data of the sensor 13 can also be regarded as positional data of the ultrasonic probe 11. The positional data of the ultrasonic probe 11 includes a position and a posture (inclination) of the ultrasonic probe 11. For example, the magnetic field transmitter 12 sequentially transmits triaxial magnetic fields and the sensor 13 sequentially receives the magnetic fields, thereby making it possible to detect the posture of the ultrasonic probe 11. The sensor 13 may be a so-called 9-axis sensor including at least one of a triaxial gyroscopic sensor for detecting a triaxial angular velocity in a three-dimensional space, a triaxial acceleration sensor for detecting a triaxial acceleration in a three-dimensional space, and a triaxial geomagnetic sensor for detecting a triaxial terrestrial magnetism in a three-dimensional space.

The main body 14 includes a transmitting and receiving circuit 21, a 2D image generation circuit 22, a 2D memory circuit 23, a positional data acquisition circuit 24, a positional data associating circuit 25, a processing circuit 26, a volume generation circuit 27, a 3D memory circuit 28, a 3D image generation circuit 29, control circuitry 30, an internal memory circuit 31, an input circuit 32, and a display 33. The transmitting and receiving circuit 21, the 2D image generation circuit 22, the positional data acquisition circuit 24, the positional data associating circuit 25, the processing circuit 26, the volume generation circuit 27, and the 3D image generation circuit 29 are composed of a field programmable gate array (FPGA) or the like.

The transmitting and receiving circuit 21 transmits an ultrasonic wave to the ultrasonic probe 11 according to a control signal from the control circuitry 30, and receives a signal (received signal) based on the ultrasonic wave received by the ultrasonic probe. The transmitting and receiving circuit 21 includes a transmission circuit which generates a drive signal for causing the ultrasonic probe 11 to radiate a transmitter pulse, and a reception circuit which performs phasing addition on the received signal from the ultrasonic probe 11.

The transmission circuit includes a rate pulse generator, a transmission delay circuit, and a pulser. The rate pulse generator generates a rate pulse for determining a repetition cycle of a transmitter pulse by dividing a continuous wave or a rectangular wave supplied from a reference signal generation circuit, and supplies the rate pulse to the transmission delay circuit. The transmission delay circuit is composed of a number of independent delay circuits corresponding to the number of transducers used for transmission. The transmission delay circuit provides the rate pulse with a delay time for focusing the transmitter pulse at a predetermined depth so as to obtain a fine beam width in the transmission, and with a delay time for radiating the transmitter pulse in a predetermined direction, and supplies the rate pulse to the pulser. The pulser includes an independent drive circuit and generates a drive pulse for driving the transducers incorporated in the ultrasonic probe 11 based on the rate pulse.

The reception circuit of the transmitting and receiving circuit 21 includes a pre-amplifier, an analog-to-digital (A/D) conversion circuit, a reception delay circuit, and an addition circuit. The pre-amplifier secures a sufficient S/N by amplifying small signals converted into electric received signals by the transducers. The received signal amplified to a predetermined size by the pre-amplifier is converted into a digital signal by the A/D conversion circuit and is transmitted to the reception delay circuit. The reception delay circuit provides the received signal output from the A/D conversion circuit with a convergence delay time for focusing a reflected wave from the predetermined depth and with a deflection delay time for setting a reception directivity in the predetermined direction. The addition circuit performs phasing addition (addition by matching the phases of received signals obtained in the predetermined direction) on the received signals from the reception delay circuit.

The 2D image generation circuit 22 generates multiple 2D image data in a chronological order, i.e., 2D image data in multiple frames, based on the received signals received from the reception circuit of the transmitting and receiving circuit 21 according to the control signal from the control circuitry 30. Examples of the type of the multiple 2D image data include B-mode image data, color mode image data, and application mode image data such as electrography.

Examples of the form of the multiple 2D image data include raw data composed of multiple raster data in the scanning surface P (shown in FIG. 2) corresponding to a certain time phase, and SC data obtained by performing scan conversion (SC) processing on raw data. A case where each piece of the multiple 2D image data is SC data obtained by performing scan conversion processing on raw data will be described below.

The 2D memory circuit 23 is a memory circuit including multiple memory cells that correspond to multiple frames and are formed in two axial directions for each frame. The 2D memory circuit 23 stores the multiple 2D image data, generated by the 2D image generation circuit 22, in a chronological order. Since the ultrasonic probe 11 is manipulated and moved by the operator, the multiple 2D image data arranged in a chronological order are data located at multiple positions. When each piece of the multiple 2D image data is raw data, time data associated with the acquisition for raster data is attached to raster data, included in each piece of the multiple raw data, by a system timer.

The positional data acquisition circuit 24 controls the magnetic field transmitter 12 to cause the magnetic field transmitter 12 to transmit a magnetic field, and acquires multiple positional data of the ultrasonic probe 11 from the sensor 13, in a chronological order. The positional data acquisition circuit 24 acquires the multiple positional data, each piece of the multiple positional data corresponding to the 2D image data, i.e., to the scanning surface for the multiple 2D image data. The positional data of the scanning surface includes the position and the posture of the scanning surface.

It is possible for the positional data acquisition circuit 24 to convert the multiple positional data of the sensor 13 into the multiple positional data of the scanning surfaces for the multiple 2D image data, based on the geometric positional relationship to each point of the scanning surface for the 2D image data.

The positional data associating circuit 25 associates the multiple positional data acquired by the positional data acquisition circuit 24 with the respective multiple 2D image data generated by the 2D image generation circuit 22. The positional data associating circuit 25 compares time data, attached to each piece of the multiple 2D image data, with time data, attached to each of the multiple positional data, and associates positional data, having a time that is closest to, immediately before, or immediately after a time of each piece of the multiple 2D image data, with the 2D image data. In this case, when each piece of the multiple 2D image data is raw data, the time of each piece of the multiple raw data may be a time attached to the first piece of the raster data among the multiple raster data comprising the each piece of the multiple raw data, a time attached to the center raster data, or an average time of the multiple raster data.

The method for matching the time of the multiple 2D image data with the time of the multiple positional data is not limited to the above method. For example, the positional data may be associated with the corresponding piece of multiple 2D image data by synchronizing the acquisition for positional data by the sensor 13 and the positional data acquisition circuit 24 with the acquisition for 2D image data.

The positional data associating circuit 25 can attach the multiple positional data to the respective multiple 2D image data so that the multiple positional data are associated with the respective multiple 2D image data. For example, the positional data associating circuit 25 writes the positional data into a header, a footer, or the like of each piece of the multiple 2D image data. The multiple 2D image data to which the respective multiple positional data is attached is stored in the 2D memory circuit 23.

In another alternative, the positional data associating circuit 25 may write the 2D image data and the positional data into a correspondence table so that the positional data is associated with each piece of the multiple 2D image data. A case where the positional data is attached to each piece of the multiple 2D image data so that the positional data is associated with each piece of the multiple 2D image data will be described below by way of example.

The processing circuit 26 performs processing in such a manner that the multiple 2D image data arranged in the 3D memory circuit 28 according to the multiple positional data fit substantially inside the memory space of the 3D memory circuit 28. In this case, the processing is one of: (1) processing in such a manner that all the multiple 2D image data stored in the 2D memory circuit 23 fit inside the memory space of the 3D memory circuit 28; and (2) processing in such a manner that all the multiple 2D image data selected from the multiple 2D image data stored in the 2D memory circuit 23 fit inside the memory space of the 3D memory circuit 28.

Figure 3:
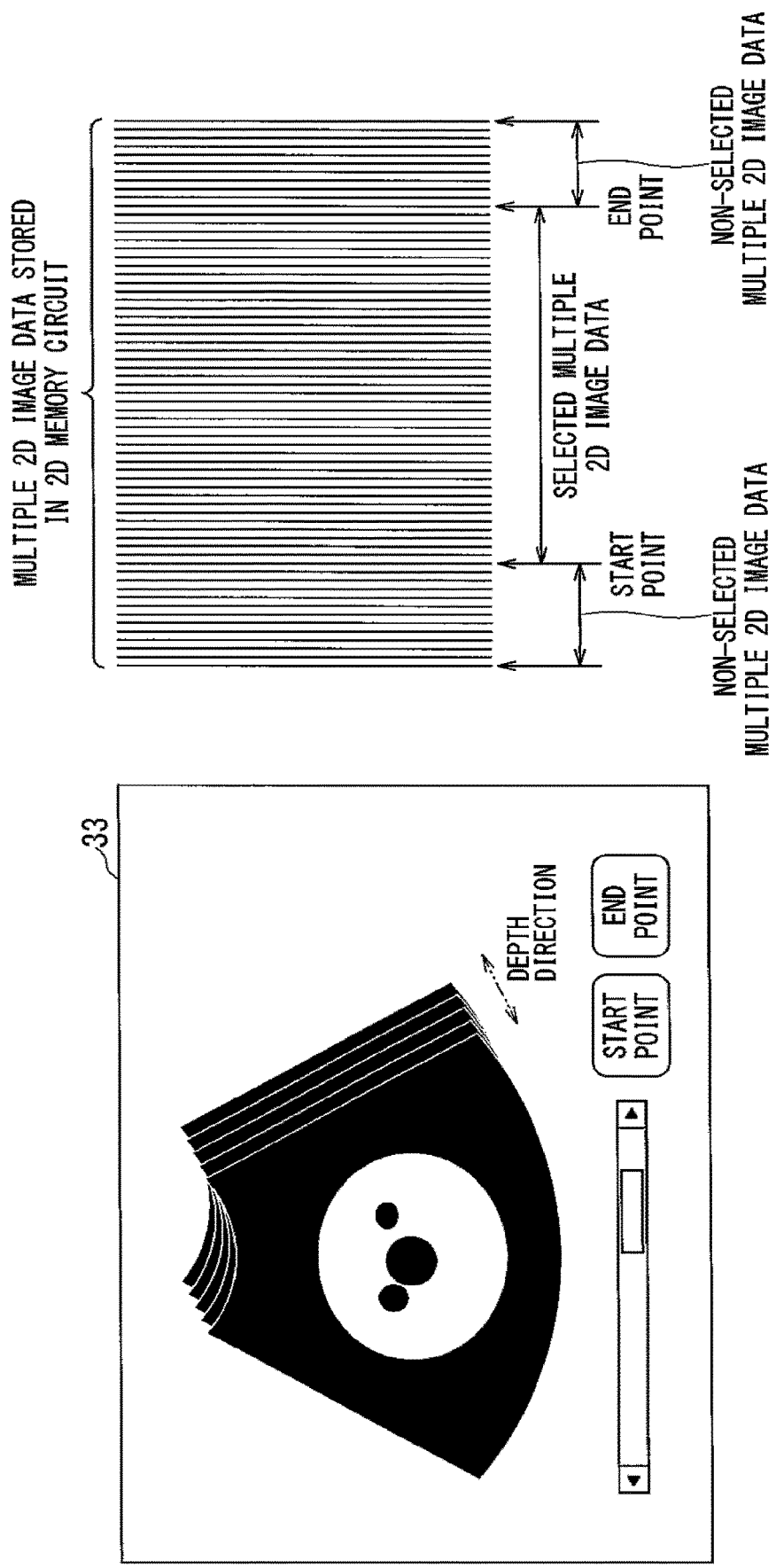
FIGS. 3A and 3B are diagrams each showing an example of a method for selecting arbitrary multiple 2D image data.

In the above-mentioned case (2), the multiple 2D image data stored in the 2D memory circuit 23 include selected multiple 2D image data and non-selected one or more pieces of 2D image data (shown in FIG. 3B). In the above-mentioned case (2), the non-selected 2D image data does not necessarily fit inside the memory space of the 3D memory circuit 28 depending on the processing. Further, in the above-mentioned case (2), the processing circuit 26 displays the multiple 2D image data stored in the 2D memory circuit 23 on the display 33 as multiple 2D images, and selects arbitrary multiple 2D image data from the displayed multiple 2D images according to an operation signal from the input circuit 32 to be described later.

FIGS. 3A and 3B are diagrams each showing an example of a method for selecting arbitrary multiple 2D image data.

As shown in FIG. 3A, the stored multiple 2D image data are displayed on the display 33 as multiple 2D images (tomographic images) in a state where the multiple 2D image data are superimposed in a depth direction. The multiple 2D images to be displayed are based on SC data obtained after scan conversion processing is performed on raw data. A scroll bar including a bar indicating the position (frame) of the forefront 2D image data among the stored multiple 2D image data is also displayed on the display 33.

The operator fixes a start point (start frame) and an end point (end frame) of a selected width by using a track ball and a hardware button as the input circuit 32 (shown in FIG. 1).

Specifically, the operator manipulates the track ball to scroll the multiple 2D images in the depth direction, thereby changing the 2D image displayed on the forefront. When the operator determines that the 2D image displayed on the forefront of the display 33 is appropriate as a start point, the operator presses the hardware button to fix the start point. After that, the operator manipulates the track ball to scroll the multiple 2D images in the depth direction, thereby changing the 2D image displayed on the forefront. When the operator determines that the 2D image which is newly displayed on the forefront of the display 33 after scrolling is appropriate as an end point, the operator presses the hardware button to fix the end point. FIG. 3B shows the concept of the multiple 2D image data selected based on the start point and the end point which are fixed in the manner described above.

The selection method is not limited to the above selection method. For example, the operator may fix the start point and the end point of the selected width by using, as the input circuit 32, a mouse and the scroll bar and button displayed on the display 33. In this case, the operator uses the mouse to slide the bar of the scroll bar on the display 33 and scroll the multiple 2D images in the depth direction, thereby changing the 2D image displayed on the forefront. When the operator determines that the 2D image displayed on the forefront of the display 33 is appropriate as a start point, the operator uses the mouse to click a "start point" button on the display 33, thereby fixing the start point. After that, the operator uses the mouse to slide the bar of the scroll bar on the display 33 and scroll the multiple 2D images in the depth direction, thereby changing the 2D image displayed on the forefront. When the operator determines that the 2D image which is newly displayed on the forefront of the display 33 after scrolling is appropriate as an end point, the operator uses the mouse to click an "end point" button on the display 33 and fixes the end point. FIG. 3B shows the concept of the multiple 2D image data selected based on the fixed start point and end point.

Referring again to FIG. 1, the processing circuit 26 performs processing, as a first example of processing, in which a magnification is calculated in such a manner that multiple 2D image data to be processed fit substantially inside the 3D memory space and the multiple 2D image data to be processed are processed at the calculated magnification. Specifically, the processing circuit 26 performs processing, as the first example of processing, in which an enlargement ratio or a reduction ratio is calculated in such a manner that the multiple 2D image data to be processed fit substantially inside the 3D memory space, and enlargement processing or reduction processing is performed on the multiple 2D image data to be processed at the calculated enlargement ratio or reduction ratio. Since the reduction processing will be described below by way of example, the terms "reduction ratio" and "reduction processing" are hereinafter used. However, it is not intended to exclude the case in which the terms "enlargement ratio" and "enlargement processing" are used. In this case, multiple 2D image data to be processed are multiple 2D image data (shown in FIG. 3B) stored in the 2D memory circuit 23, or multiple 2D image data (shown in FIG. 3B) selected from the multiple 2D image data stored in the 2D memory circuit 23, and are hereinafter referred to as a "2D image data set".

The processing circuit 26 preferably adopts the reduction ratio obtained when the 2D image data set fits inside the 3D memory space and the size (magnitude) of the 2D image data set is maximum. The reduction processing in the processing circuit 26 will be described later mainly with reference to FIGS. 6A to 8.

The processing circuit 26 performs processing, as a second example of processing, in which an orientation for the 2D image data set is calculated in such a manner that the 2D image data set fits substantially inside the 3D memory space and orientation change processing is performed on the 2D image data set according to the calculated orientation. When the 2D image data set fits inside the 3D memory space after the orientation change processing, the processing circuit 26 may enlarge the 2D image data set so that the size of the 2D image data set subjected to the orientation change processing becomes maximum. In other words, the processing circuit 26 may calculate an orientation in which the size of the 2D image data set becomes maximum, by giving priority over the size of the 2D image data set. The orientation change processing in the processing circuit 26 will be described later mainly with reference to FIGS. 9A and 9B.

The processing circuit 26 performs, as a third example of processing, a combined processing of orientation change processing and reduction processing on a 2D image data set.

The processing circuit 26 calculates an appropriate orientation for the 2D image data set, and performs orientation change processing on the 2D image data set according to the calculated orientation. Subsequently, the processing circuit 26 calculates a reduction ratio in such a manner that the 2D image data set subjected to the orientation change processing fits substantially inside the memory space, and performs reduction processing on the 2D image data set subjected to the orientation change processing at the reduction ratio. The processing circuit 26 preferably adopts a data set including the reduction ratio at which the size of the 2D image data set becomes maximum. A combined processing of orientation change processing and reduction processing in the processing circuit 26 will be described later mainly with reference to FIGS. 10A to 11D.

The volume generation circuit 27 performs three-dimensional reconstruction for performing interpolation processing, as needed, on the 2D image data set which is processed by the processing circuit 26 and is arranged in the 3D memory circuit 28, thereby generating volume data in the 3D memory circuit 28. A well-known technique is used as the interpolation processing method. Examples of the well-known technique include a technique disclosed by Trobaugh, J. W., Trobaugh, D. J., Richard W. D. "Three-Dimensional Imaging with Stereotactic Ultrasonography", Computerized Medical Imaging and Graphics, 18: 5, 315-323, 1994 (hereinafter referred to as "Non-Patent Literature").

In the technique disclosed in Non-Patent Literature, 2D image data corresponding to adjacent two frames are arranged in a space using positional data, and a pixel value on a surface between the data is calculated from the value of a proximal point (pixel) by interpolation such as nearest neighbor, bilinear interpolation, or bicubic interpolation.

The volume generation circuit 27 corrects the acquired multiple positional data in accordance with the processing result by the processing circuit 26, and generates volume data, based on multiple 2D image data arranged according to the corrected multiple positional data, using the technique disclosed in Non-Patent Literature.

The 3D memory circuit 28 is a memory circuit including multiple memory cells in three axial directions (X-axis, Y-axis, and z-axis directions). The 3D memory circuit 28 stores the volume data generated by the volume generation circuit 27.

Figure 4:
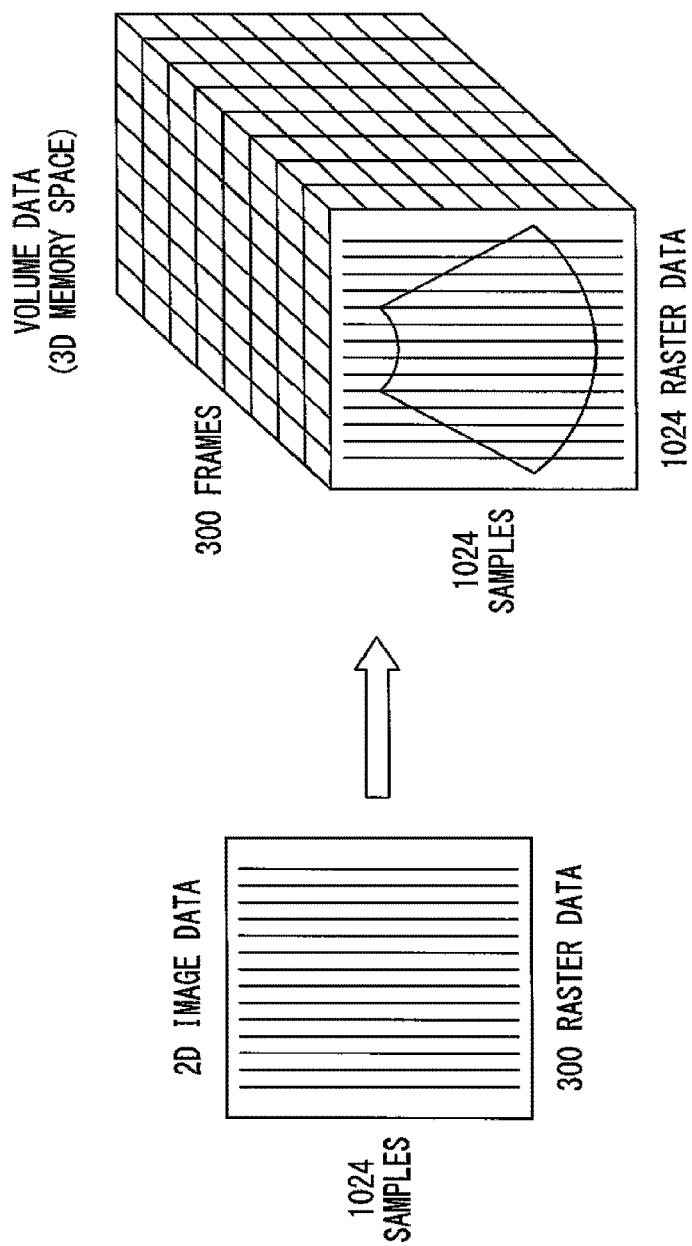
FIG. 4 is a diagram showing a relationship between a 3D memory space and the volume data.

FIG. 4 is a diagram showing a relationship between the 3D memory space and the volume data.

A case where a convex scanning system is employed as the scanning system of the ultrasonic probe 11 will be described by way of example. The 2D image data shown on the left side of FIG. 4 is raw data, and thus the data do not have a fan-like form. The raw data includes multiple raster data, for example, 300 pieces of raster data.

As shown on the right side of FIG. 4, the volume data has a raw data format and includes multiple frames in the depth direction. Each frame of the volume data has a fan-like form, like SC data. Specifically, when the convex scanning system is employed, the volume data has a format like raw data of a linear probe, and includes convex data in the 3D memory space of the 3D memory circuit 28.

For example, a value "0" is set in a memory cell that is outside of the convex shape in the 3D memory space and includes no data. Since the existing renderer reads raw data as an input, when the volume data is included in the format of raw data, the existing renderer can be applied as it is. In addition, when a data region is formed into a square shape so as to match the shape of a display region, the data region can be efficiently secured.

To facilitate explanation, a region in which data is actually included in the convex shape and the volume data is generated is hereinafter referred to as a "2D image data set" obtained before three-dimensional reconstruction is performed, and a rectangular parallelepiped region including the memory cell which indicates "0" and includes no data is hereinafter referred to as a "3D memory space". Thus, these regions are distinguished from each other. In this case, the number of samples, the number of rasters, and the number of frames in the 2D image data set are generally different from those in the 3D memory space. For example, in FIG. 4, the number of samples in the 2D image data set is 1024; the number of rasters in the 2D image data set is 300; the number of samples in the 3D memory space is 1024; the number of rasters in the 3D memory space is 1024; and the number of frames in the 3D memory space is 300. Assuming that the data length of one pixel is one byte (1B), the capacity of the 3D memory space is represented as 300 MB (1B*1024sample*1024raster*300fr).

Referring back to FIG. 1, the 3D image generation circuit 29 performs 3D image processing, such as MPR (Multi-Planar Reconstruction) processing, volume rendering processing, surface rendering processing, and MIP (Maximum Intensity Projection) processing, on the volume data stored in the 3D memory circuit 28. Further, the 3D image generation circuit 29 performs 3D image processing on the volume data, thereby generating 3D image data such as MPR image data, volume rendering image data, surface rendering image data, and MIP image data. Furthermore, the 3D image generation circuit 29 displays the 3D image data on the display 33 as a 3D image.

The control circuitry 30 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The control circuitry 30 reads out a program, which is stored in the internal memory circuit 31 or is directly incorporated into the control circuitry 30, and executes the program, thereby comprehensively controlling the processing operations of the units 21 to 29 and 31 to 33.

The control circuitry 30 may be a single processing circuit or a combination of multiple processing circuit elements. In the latter case, the internal memory circuit 31 includes multiple memory circuit elements each storing an element of a program that the control circuitry 30 executes, and each corresponding to the processing circuit element.

Alternatively, in the latter case, the internal memory circuit 31 includes a single memory circuit storing the program that the control circuitry 30 executes, and corresponding to the processing circuit element.

The internal memory circuit 31 is composed of a semiconductor memory element, such as a RAM (random access memory) or a flash memory, a hard disk, an optical disk, or the like. The internal memory circuit 31 may be composed of a portable medium such as a USB (universal serial bus) memory, or a DVD (digital video disk). The internal memory circuit 31 stores various processing programs (including an application program, as well as an OS (operating system)) used in the control circuitry 30, and data necessary for executing the programs. The OS may include a GUI (graphical user interface) with which basic operations can be performed by the input circuit 32 by making great use of graphics for a display of information for the operator on the display 33.

The input circuit 32 is a circuit which inputs a signal from an input device that is operable by the operator. In this case, the input device itself is included in the input circuit 32. The input device includes a pointing device (such as a mouse), a keyboard, a track ball, and various buttons. When the input device is manipulated by the operator, the input circuit 32 generates an input signal according to the manipulation and outputs the input signal to the control circuitry 30. The main body 14 may include a touch panel having a configuration in which the input device is integrated with the display 33.

The input circuit 32 outputs a transmission condition set by the operator to the control circuitry 30. Examples of the transmission condition include a center frequency of an ultrasonic wave transmitted through the ultrasonic probe 11.

The center frequency varies depending on a sweep system (linear, convex, sector, etc.), a region to be diagnosed of a subject, an ultrasonic diagnosis mode (such as B-mode, Doppler mode, and color Doppler mode), a distance from the surface of the subject to the region to be diagnosed, or the like.

The input circuit 32 includes a button that is operable by the operator to start data acquisition, a button for terminating the data acquisition, and a switch for switching whether or not to perform the process by the processing circuit 26.

The display 33 includes a general display output device such as a liquid crystal display or an OLED (organic light emitting diode) display. The display 33 displays, as a 3D image, the 3D image data generated by the 3D image generation circuit 29 or the like by the control of the control circuitry 30.

The processing performed by the processing circuit 26 will be described with reference to FIGS. 5A to 11D. FIGS. 5A to 5E are diagrams showing types of sweep formats used by the ultrasonic probe 11.

FIGS. 5A to 5E show five types of sweep formats. In any one of the sweep formats, three-dimensional reduction processing is performed on the 2D image data set in such a manner that the 2D image data set fits inside the 3D memory space of the 3D memory circuit 28.

The reduction processing performed by the processing circuit 26 will be described with reference to FIGS. 6A to 8.

Figure 6B:
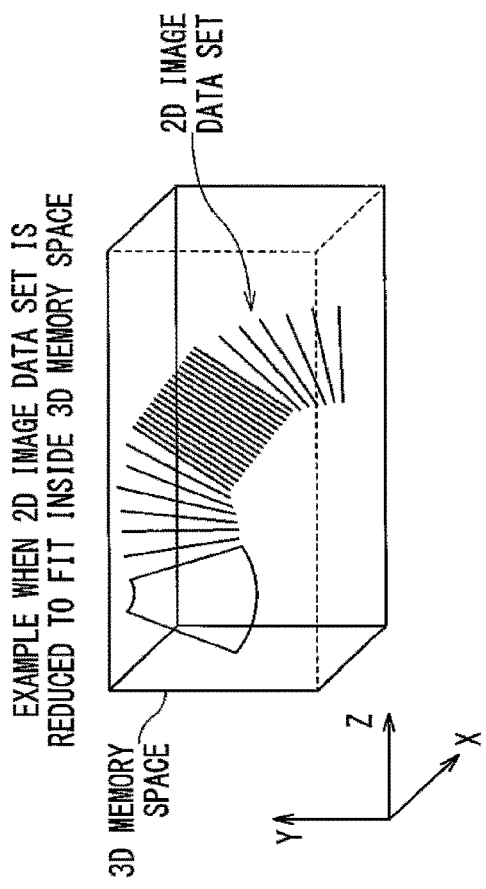
FIGS. 6A and 6B are conceptual diagrams each showing a reduction processing performed by a processing circuit.
Figure 6A:
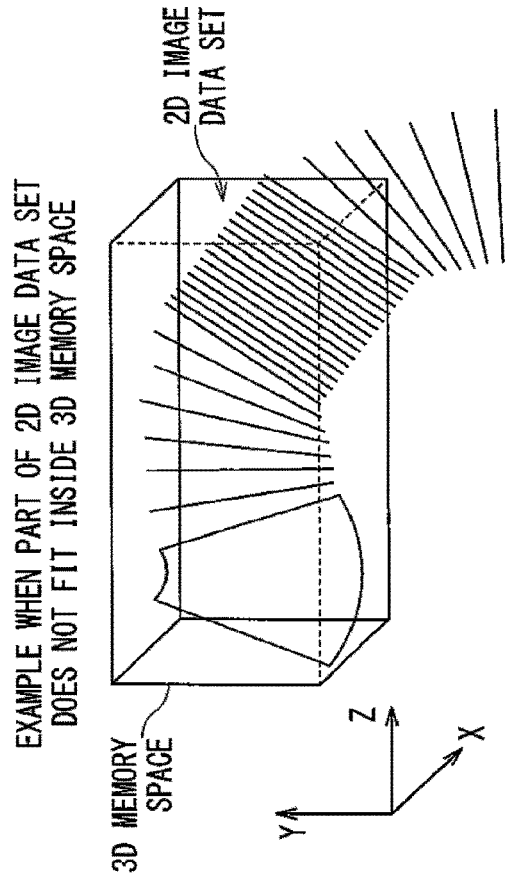

FIGS. 6A and 6B are conceptual diagrams each showing the reduction processing performed by the processing circuit 26.

To facilitate explanation, the 2D image data set is hereinafter illustrated as an SC data format. Depending on the relationship between the 3D memory space of the 3D memory circuit 28 and the size of the 2D image data set, a part of the 2D image data set arranged according to the multiple positional data does not fit inside the 3D memory space in some cases (FIG. 6A). In this case, the volume data based on the 2D image data set in which a part of the data is missing is generated. This results in deterioration of diagnostic capabilities due to the 3D image based on the volume data.

Accordingly, when a part of the 2D image data set does not fit inside of the 3D memory space, the reduction ratio at which the entire 2D image data set fits inside the 3D memory space of the 3D memory circuit 28 is calculated, and three-dimensional reduction processing is performed on the 2D image data set at the reduction ratio (FIG. 6B). This allows the entire 2D image data set to fit inside the 3D memory space. In other words, the 3D image which is based on the volume data based on the entire 2D image data set can be displayed, which leads to an improvement in diagnostic capabilities.

The reduction ratio in the reduction processing performed on the 2D image data set will now be described.

Figure 7B:
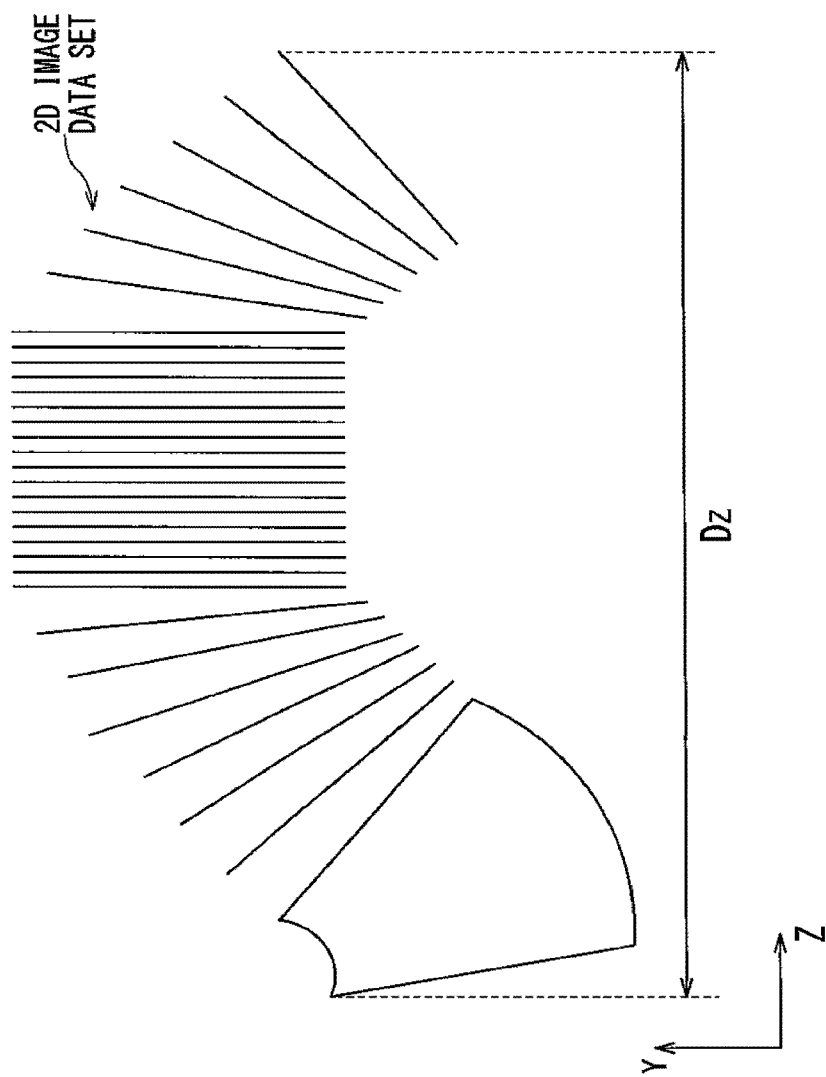
FIGS. 7A and 7B are diagrams for explaining a reduction ratio for a 2D image data set.
Figure 7A:
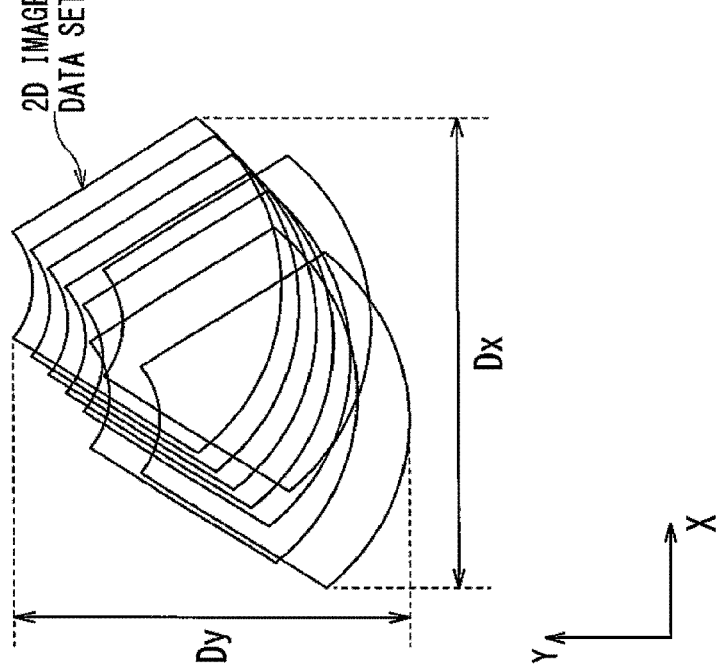

FIGS. 7A and 7B are diagrams for explaining the reduction ratio for the 2D image data set.

FIG. 7A is a front view of the 2D image data set, and shows an X-Y plane of the 3D memory space. FIG. 7B is a side view of the 2D image data set and shows a Z-Y plane of the 3D memory space. In FIGS. 7A and 7B, the extents of the 2D image data set in the X-axis, Y-axis, and Z-axis directions in the 3D memory space are defined as Dx, Dy, and Dz, respectively.

The reduction processing in the X-Y plane of the 3D memory space will be described with reference to FIG. 7A. Assume that the sample pitch on the X-Y plane (frame surface) of the 3D memory space is equal to the raster pitch. For example, if Dx>Dy holds, reduction processing is performed on the 2D image data set with the same magnification in the X-axis and Y-axis directions in such a manner that Dx is fully extended to the both ends of the raster. In this case, the size of Dy is smaller than the length in the Y-axis direction of the 3D memory space so that spaces are formed above and below Dy. The position of each point of each piece of multiple 2D image data on the scanning surface is converted from the position and posture of the ultrasonic probe 11 as described above.

In general, the sample pitch may be different from the raster pitch, and the reduction processing of Dx may be performed with a magnification different from that of the reduction processing of Dy. In this case, Dx may be fully extended to the both ends of the raster so that the size of Dy becomes equal to the length in the Y-axis direction of the 3D memory space.

Figure 8:
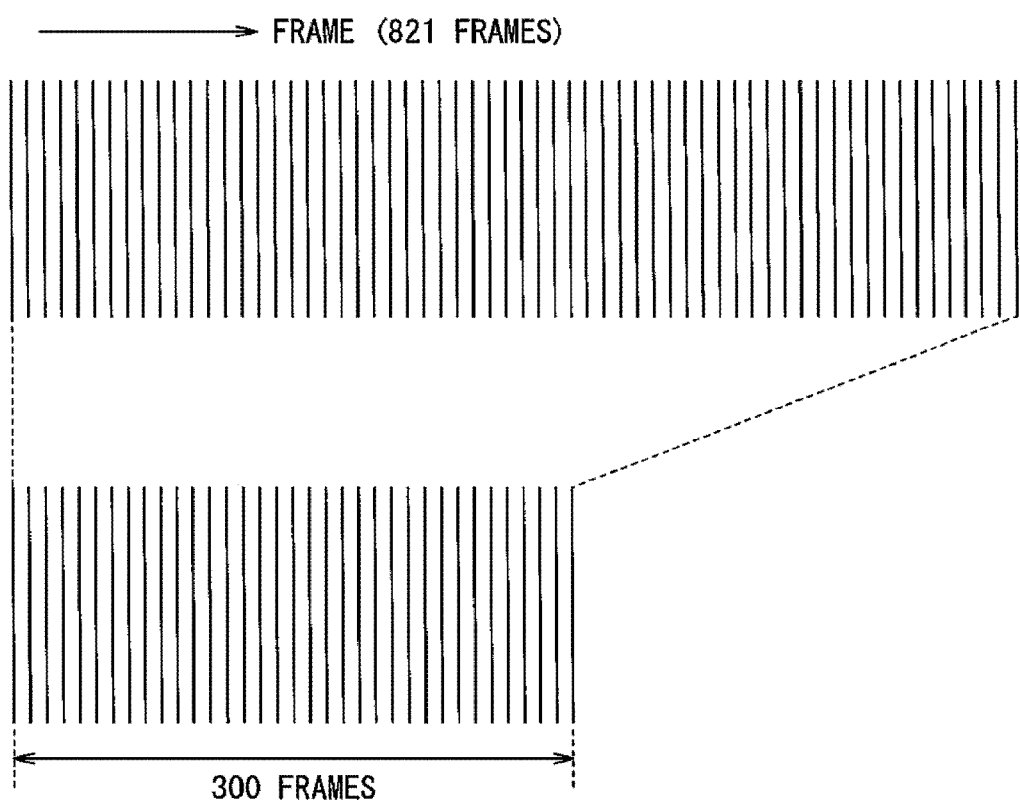
FIG. 8 is a diagram for explaining a reduction processing in a Z-axis direction of the 3D memory space.

FIG. 8 is a diagram for explaining reduction processing in the Z-axis direction of the 3D memory space.

When the frame size (the number of frames) of the volume data three-dimensionally constructed from multiple 2D image data to be processed that constitute the 2D image data set exceeds the frame size in the Z-axis direction of the 3D memory space of the 3D memory circuit 28 (as shown in the upper part of FIG. 8), the frame pitch is widened. The reduction processing is performed so as to prevent Dz of the 2D image data set (FIG. 7B) from exceeding the frame size in the Z-axis direction of the 3D memory space. For example, in the upper part of FIG. 8, when the sample pitch is 0.146 [mm], the depth is 15 [cm], and the number of samples is 1024[samples], the frame pitch may be generally larger than the sample pitch in consideration of a spatial resolution of an ultrasonic wave, and the frame pitch is not necessarily smaller than 0.146 [mm].

In an initial setting, when the length of the volume data is 12 [cm], the frame pitch is 0.146 [mm], and the number of frames is 821[fr (12 cm/0.146 mm)], the size of the volume data is 821 [MB (1B*1024sample*1024raster*821fr)]. In this case, the size 821 [MB] of the volume data exceeds the memory size 300 [MB] of the 3D memory space, and thus the reduction processing of the 2D image data set is required. Accordingly, when the reduction processing is performed on the 2D image data set assuming that the reduction ratio is 300 [MB]/821 [MB](=0.365), the length of the volume data obtained by three-dimensionally reconstructing the 2D image data set subjected to the reduction processing is 12 [cm]; the frame pitch is 0.400 [mm (0.146 [mm]/0.365)]; the number of frames is 300[fr (821fr*0.365)]; and the size of the volume data is 300 [MB (1B*1024sample*1024raster*300fr)]. In other words, the size 300 [MB] of the volume data obtained by three-dimensionally reconstructing the 2D image data set subjected to the reduction processing does not exceed the size 300 [MB] of the memory of the 3D memory space.

In this manner, the reduction processing in the Z-axis direction can be performed independently of the reduction processing in the X-Y plane. In general, the frame pitch in the Z-axis direction is different from the sample pitch and the raster pitch in the X-Y plane. However, the frame pitch, the sample pitch, and the raster pitch may be the same. In this case, the widest pitch among the three pitches is adopted.

As described above, the processing circuit 26 performs the reduction processing on the 2D image data set, so that the 2D image data set fits inside the 3D memory space with no missing data, thereby making it possible to provide an ultrasonic diagnostic apparatus with high diagnostic capabilities.

Next, the orientation change processing performed by the processing circuit 26 will be described with reference to FIGS. 9A to 9B.

FIGS. 9A and 9B are conceptual diagrams showing the orientation change processing performed by the processing circuit 26.

Depending on the relationship between the 3D memory space of the 3D memory circuit 28 and the size of the 2D image data set, a part of the 2D image data set arranged according to the multiple positional data does not fit inside of the 3D memory space in some cases (FIG. 9A). In this case, the volume data based on the 2D image data set in which a part of the data is missing is generated. This results in deterioration of diagnostic capabilities due to the 3D image based on the volume data.

Accordingly, when a part of the 2D image data set does not fit inside of the 3D memory space, the orientation for the 2D image data set is calculated in such a manner that the 2D image data set fits inside the 3D memory space of the 3D memory circuit 28, and three-dimensional orientation change processing is performed on the 2D image data set in the orientation (FIG. 9B). Specifically, an orientation G1 of the 2D image data corresponding to a head frame included in the 2D image data set is changed to an orientation G2, to thereby change the orientation for the 2D image data set. A position H1 of the 2D image data corresponding to the head frame in the 3D memory circuit 28 before changing the orientation is shifted to a position H2 by the orientation change processing to the orientation G2 in which the 2D image data set fits inside the 3D memory space of the 3D memory circuit 28. This allows the entire 2D image data set to fit inside the 3D memory space. In other words, the 3D image which is based on the volume data based on the entire 2D image data set can be displayed, which leads to an improvement in diagnostic capabilities.

After performing the above-mentioned orientation change processing, the processing circuit 26 may further perform the reduction processing on the 2D image data set subjected to the orientation change processing.

Next, a combined processing of orientation change processing and reduction processing performed by the processing circuit 26 will be described with reference to FIGS. 10A to 11D.

Figure 10A:
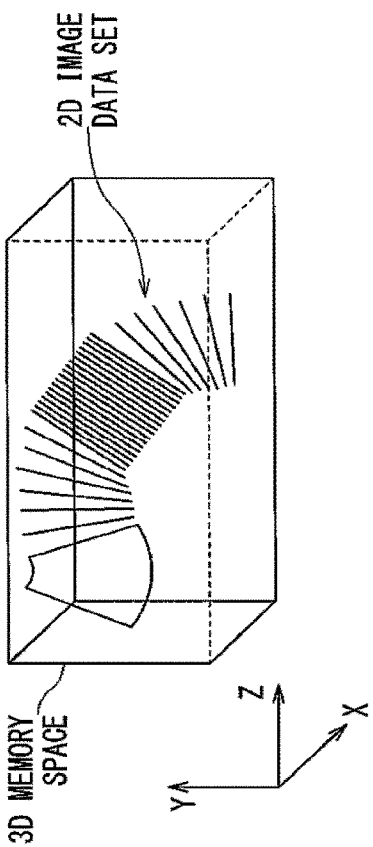
FIGS. 10A to 10C are conceptual diagrams showing a combined processing of orientation change processing and reduction processing performed by the processing circuit.
Figure 10B:
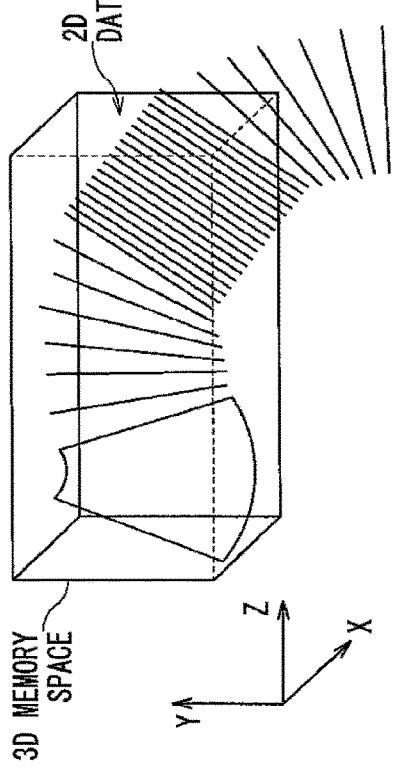
Figure 10C:
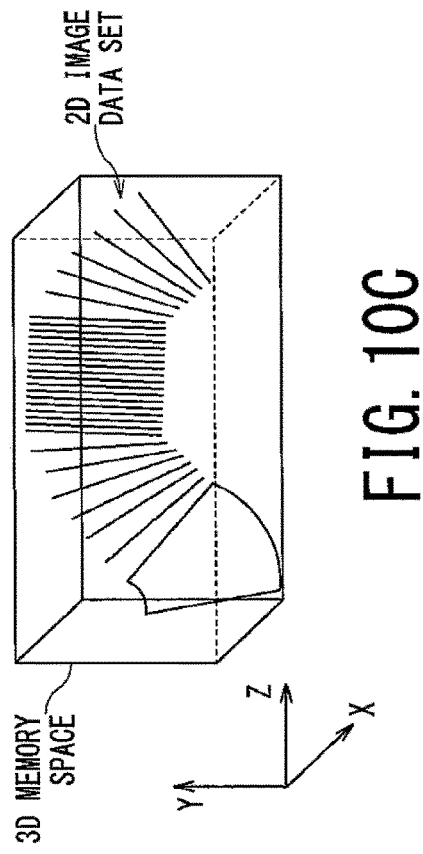

FIGS. 10A to 10C are conceptual diagrams showing the combined processing of orientation change processing and reduction processing performed by the processing circuit 26.

FIGS. 10A and 10B are identical with FIGS. 6A and 6B, respectively. When a part of the 2D image data set does not fit inside of the 3D memory space of the 3D memory circuit 28, the orientation for the 2D image data set is appropriately adjusted three-dimensionally, and then three-dimensional reduction processing is performed so that the 2D image data set fits inside the 3D memory space (FIG. 10C). Thus, unlike in the case of FIG. 10A, the 2D image data set fits inside the 3D memory space, and unlike in the case of FIG. 10B, the spatial resolution is appropriately set. In other words, since the 3D image based on the volume data with an appropriate spatial resolution can be displayed based on the entire 2D image data set, diagnostic capabilities are further improved.

The orientation change processing of the 2D image data set in the combined processing of the orientation change processing and the reduction processing will now be described.

FIGS. 11A to 11D are diagrams for explaining a method for setting the orientation for the 2D image data set in the combined processing.

Figure 11C:
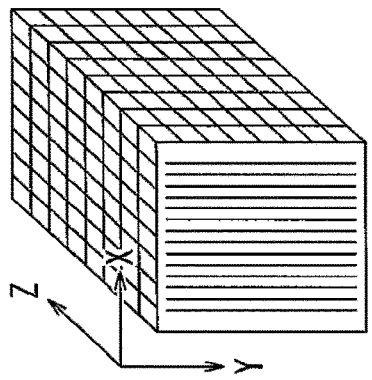
FIGS. 11A to 11D are diagrams for explaining a method for setting an orientation for the 2D image data set in the combined processing.
Figure 11B:
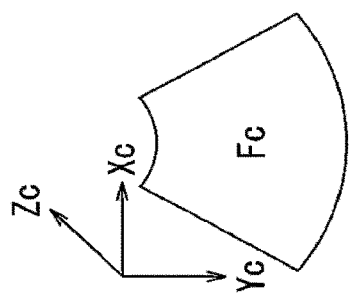
Figure 11A:
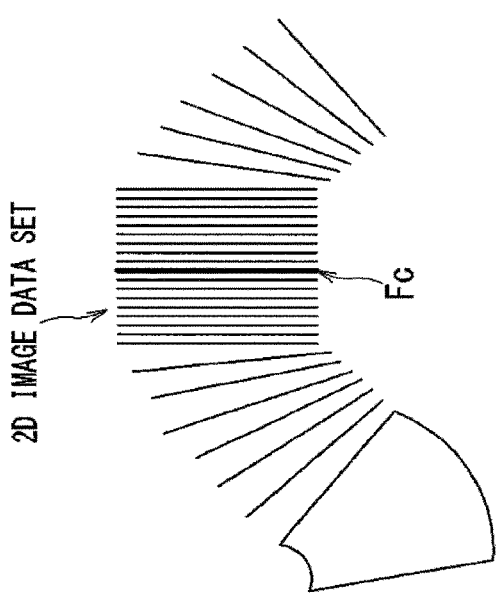
Figure 11D:
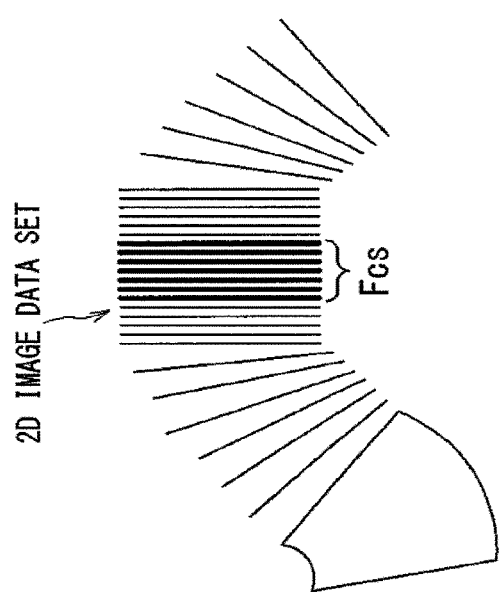

FIG. 11A shows 2D image data sets arranged according to the multiple positional data. From the 2D image data set, 2D image data Fc in a center frame is selected. For example, when the 2D image data corresponding to 200 frames are acquired, the center frame is the 100th frame. The orientation for 2D image data Fc is set as the orientation for the 2D image data set. Specifically, Xc, Yc, and Zc axes of the 2D image data Fc shown in FIG. 11B are respectively set as the X-axis, the Y-axis, and the Z-axis of the 2D image data set, and are respectively set as an X-axis, a Y-axis, and a Z-axis of the 3D memory space shown in FIG. 11C. There is no need to match the origins.

Note that the orientation for the 2D image data set subjected to the orientation change processing may be inappropriate due to shaking or the like of the 2D image data Fc shown in FIG. 11A, for example, in a case where the 2D image data Fc is obtained when the ultrasonic probe 11 is unintentionally tilted. In this case, for 2D image data Fcs (FIG. 11D) corresponding to several frames, for example, seven frames, in the vicinity of the center frame, the orientations for the respective 2D image data sets are calculated and a median thereof is set as the orientation for the 2D image data set.

As described above, the processing circuit 26 appropriately adjusts the orientation for the 2D image data set and then performs the reduction processing on the 2D image data set, so that a vacant space in the 3D memory space can be reduced and the 3D image data can be increased. In addition, the spatial resolution of the 3D image data can be set as high as possible, which leads to a further improvement in diagnostic capabilities.

Next, an operation of the ultrasonic diagnostic apparatus 10 will be described with reference to FIGS. 1 and 12.

Figure 12:
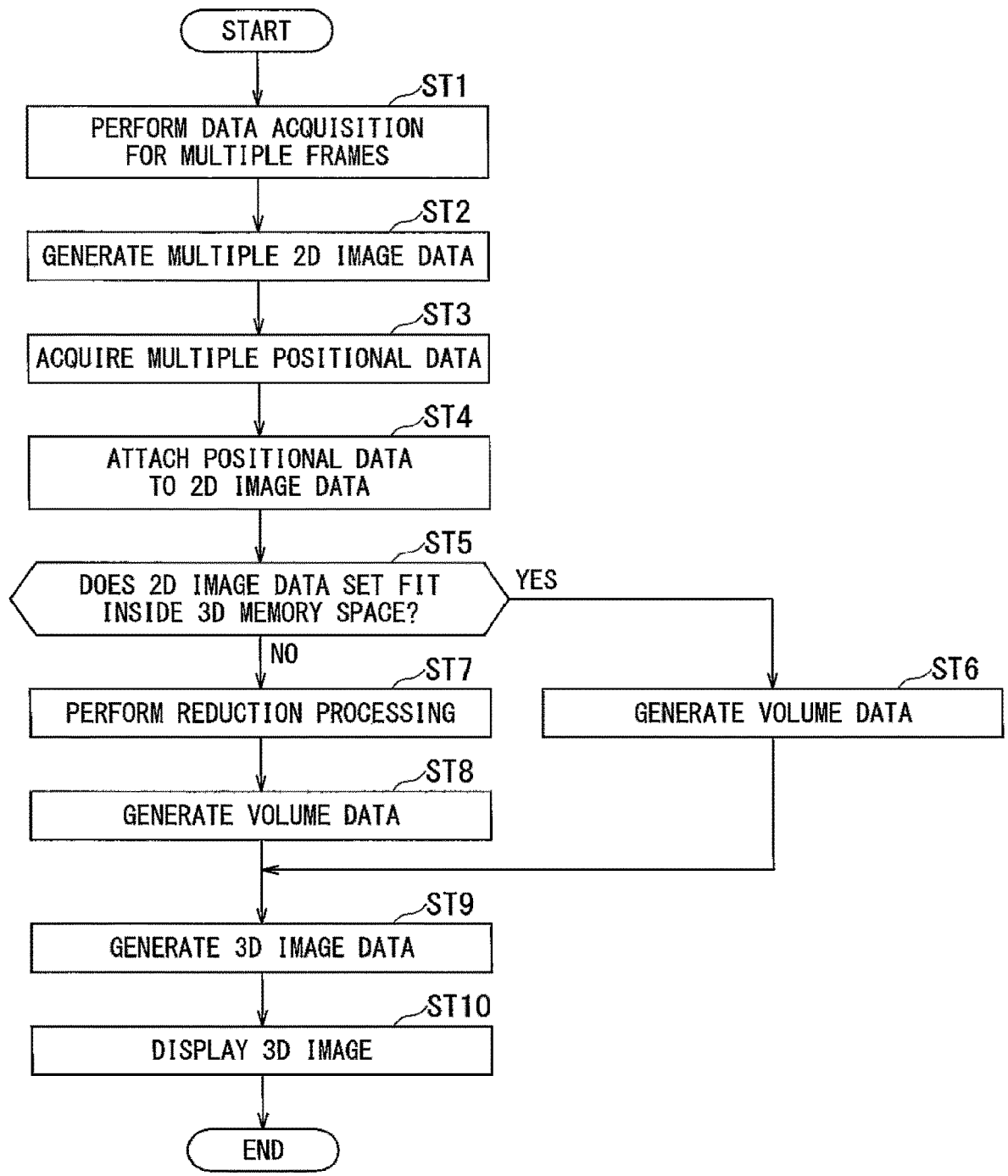
FIG. 12 is a flowchart showing an operation of the ultrasonic diagnostic apparatus.

FIG. 12 is a flowchart showing an operation of the ultrasonic diagnostic apparatus 10. FIG. 12 illustrates a case where the processing circuit 26 performs the reduction processing on the 2D image data set.

When the button for starting the data acquisition as the input circuit 32 is pressed by the operator, the transmitting and receiving circuit 21 controls the ultrasonic probe 11 to execute ultrasonic waves transmitting and receiving, and performs data acquisition for multiple frames (step ST1). The 2D image generation circuit 22 generates multiple 2D image data in a chronological order based on the data acquired in step ST1 (step ST2).

The positional data acquisition circuit 24 acquires the multiple positional data of the ultrasonic probe 11 from the sensor 13, each of the multiple positional data corresponding to each piece of the multiple 2D image data (step ST3). The positional data associating circuit 25 attaches the positional data acquired in step ST3 to each piece of the multiple 2D image data generated in step ST2 (step ST4). The multiple 2D image data to which the positional data is attached in step ST4 is stored in the 2D memory circuit 23.

The processing circuit 26 determines whether or not the 2D image data set arranged in the 3D memory circuit 28 according to the multiple positional data attached by the positional data associating circuit 25 fits inside the 3D memory space of the 3D memory circuit 28 (step ST5). In step ST5, the processing circuit 26 matches the orientation for the 2D image data corresponding to the head frame in the 2D image data set with the orientation for the 3D memory space, and appropriately arranges the 2D image data corresponding to the subsequent frames. Then, the processing circuit 26 determines whether or not the 2D image data set fits inside the 3D memory space. As described above, the 2D image data set indicates multiple 2D image data to be processed, multiple 2D image data (shown in FIG. 3B) stored in the 2D memory circuit 23, or multiple 2D image data (shown in FIG. 3B) selected from the multiple 2D image data stored in the 2D memory circuit 23.

In the case of YES in the determination of step ST5, that is, when it is determined that the 2D image data set fits inside the 3D memory space of the 3D memory circuit 28, the volume generation circuit 27 performs three-dimensional reconstruction for performing interpolation processing, as needed, on the 2D image data set arranged in the 3D memory circuit 28 according to related art, thereby generating volume data in the 3D memory circuit 28 (step ST6).

On the other hand, in the case of NO in the determination of step ST5, that is, when it is determined that a part of the 2D image data set does not fit inside of the 3D memory space of the 3D memory circuit 28, the processing circuit 26 performs the reduction processing on the 2D image data set (step ST7). The reduction processing in step ST7 is described above with reference to FIGS. 6A to 8.

The volume generation circuit 27 performs three-dimensional processing for performing interpolation processing, as needed, on the 2D image data set, which is subjected to the reduction processing and arranged in the 3D memory circuit 28, thereby generating volume data in the 3D memory circuit 28 (step ST8).

The 3D image generation circuit 29 performs the 3D image processing on the volume data generated in the 3D memory circuit 28 in step ST6 or ST8, thereby generating 3D image data (step ST9). Further, the 3D image generation circuit 29 displays the 3D image data on the display 33 as a 3D image (step ST10).

The ultrasonic diagnostic apparatus 10 performs processing in such a manner that the 2D image data set arranged in the 3D memory 28 according to the multiple positional data fits substantially inside the memory space of the 3D memory circuit 28, thereby making it possible to improve diagnostic capabilities using a 3D image to be displayed based on the 2D image data set. Further the ultrasonic diagnostic apparatus 10 adjusts the orientation for the 2D image data set and then performs the reduction processing on the adjusted 2D image data set so as to take into consideration a spatial resolution, thereby making it possible to further improve diagnostic capabilities using the 3D image to be displayed based on the 2D image data set.

2. First Modified Example

As described above with reference to FIG. 4, the frames in the 3D memory space of the 3D memory circuit 28 are formed into a format like raw data of a linear probe. However, another method may be employed. That is, the number of samples in the 3D memory space and the number of rasters are set to be the same as those of the 2D image data (raw data), and the frames of the 3D memory space are treated in the same manner as the 2D image data. This method has an advantage that the header and footer of 2D image data can be used as they are. However, in this method, when the frames of the 3D memory space are read by a renderer, for example, the frames are developed into a convex shape, and the display range is limited to the developed convex region.

3. Second Modified Example

The case where the reduction ratio for the 2D image data set is calculated in the orientation for the 2D image data set that is determined based on the 2D image data Fc in the center frame has been described above with reference with FIG. 11A. Further, the case where the reduction ratio for the 2D image data set is calculated in the orientation for the 2D image data set that is determined based on the 2D image data Fcs in multiple frames including the center frame has been described above with reference to FIG. 11D. However, the present invention is not limited to these cases. The processing circuit 26 may perform the reduction processing and the orientation change processing on the 2D image data set based on a minimum reduction ratio (minimum reduction) and the corresponding orientation.

Specifically, the processing circuit 26 determines multiple orientations for spaced multiple 2D image data in the 2D image data set. The processing circuit 26 calculates multiple reduction ratios when the orientation change processing is performed on the 2D image data set according to the multiple orientations. In this case, each reduction ratio indicates a reduction ratio when the 2D image data set fits inside the 3D memory space. The processing circuit 26 adopts a minimum value among the multiple reduction ratios as the reduction ratio, performs the orientation change processing on the 2D image data set according to an orientation corresponding to the minimum value, and performs the reduction processing on the 2D image data set at a reduction ratio corresponding to the minimum value.

Figure 13:
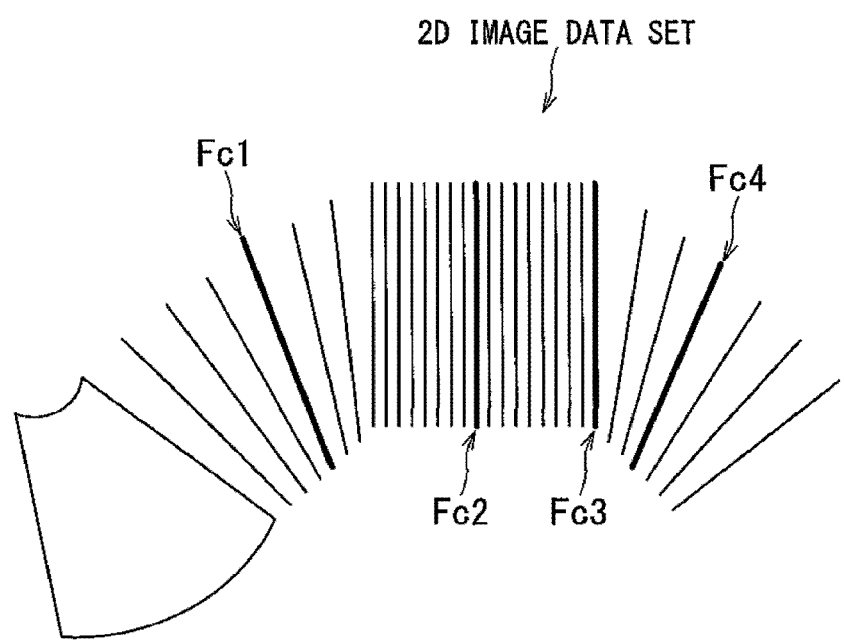
FIG. 13 is a diagram showing spaced multiple 2D image data in the 2D image data set.

FIG. 13 is a diagram showing spaced multiple 2D image data in the 2D image data set.

As shown in FIG. 13, four pieces of spaced 2D image data Fc1 to Fc4 included in the 2D image data set are set. In four orientations for the 2D image data set that are determined based on the four pieces of 2D image data Fc1 to Fc4, respectively, four reduction ratios are calculated and a minimum value among the four reduction ratios is adopted as the reduction ratio for the 2D image data set. In this case, the orientation corresponding to the minimum value is adopted as the orientation for the 2D image data set.

Thus, since the spatial resolution is taken into consideration, diagnostic capabilities using the 3D image to be displayed based on the 2D image data set can be further improved.

The processing circuit 26 may perform enlargement processing and orientation change processing on the 2D image data set based on a maximum enlargement ratio (maximum enlargement) and the orientation corresponding to the maximum enlargement ratio. In this case, the processing circuit 26 determines multiple orientations for spaced multiple 2D image data in the 2D image data set. The processing circuit 26 calculates multiple enlargement ratios when the orientation change processing is performed on the 2D image data set according to the multiple orientations. In this case, each enlargement ratio indicates an enlargement ratio when the 2D image data set fits inside the 3D memory space. The processing circuit 26 adopts a maximum value among the multiple enlargement ratios as the enlargement ratio, performs the orientation change processing on the 2D image data set according to the orientation corresponding to the maximum value, and performs the enlargement processing on the 2D image data set at the enlargement ratio corresponding to the maximum value.

4. Third Modified Example

The embodiments described above assume a case where the reduction processing is performed after the acquisition for 2D image data is finished, to thereby generate and display volume data. However, the present invention is not limited to this case. For example, the reduction processing may be performed while 2D image data are acquired, to thereby generate and display volume data in real time. In this case, the processing of the present invention is performed at each point during acquisition by using the acquired 2D image data.

There is a method of updating the processing of the present invention every time a frame of the 2D image data is added. However, in order to avoid an increase in load on the device, there is a simple method of updating the processing when the 2D image data falls outside of the frames in the X-axis, Y-axis, Z-axis directions of the 3D memory space shown in FIG. 10A. There is a simpler method of increasing the reduction ratio, without optimizing the reduction ratio, when the 2D image data falls outside of the frame in the Z-axis direction, and continuously giving a margin to the memory in the Z-axis direction.

5. Medical Image Processing Apparatus According to a Present Embodiment

Figure 14:
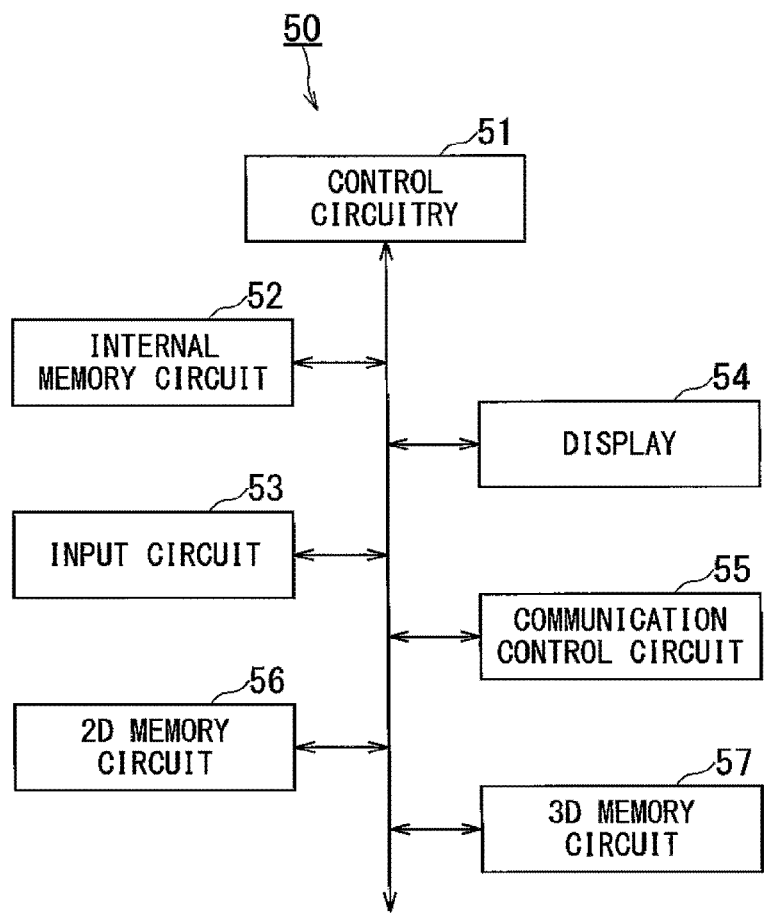
FIG. 14 is a schematic diagram showing a configuration of a medical image processing apparatus according to a present embodiment.

FIG. 14 is a schematic diagram showing a configuration of a medical image processing apparatus according to a present embodiment.

FIG. 14 shows a medical image processing apparatus 50 according to the present embodiment. The medical image processing apparatus 50 is, for example, a medical image management device (image server), which is not shown, a workstation, or a diagnostic reading terminal, which is not shown, and is provided on a medical image system connected via a network. The medical image processing apparatus 50 may be an offline device.

The medical image processing apparatus 50 includes control circuitry 51, an internal memory circuit 52, an input circuit 53, a display 54, a communication control circuit 55, a 2D memory circuit 56, and a 3D memory circuit 57.

The control circuitry 51 has a configuration similar to that of the control circuitry 30 shown in FIG. 1. The control circuitry 51 reads out a program which is stored in the internal memory circuit 52 or is directly incorporated into the control circuitry 51, and executes the program, thereby comprehensively controlling the processing operation of the units 52 to 57.

The internal memory circuit 52 has a configuration similar to that of the internal memory circuit 31 shown in FIG. 1. The internal memory circuit 52 stores various processing programs used in the control circuitry 51 and data necessary for executing the programs. The OS may include a GUI capable of performing basic operations by the input circuit 53 by making great use of graphics for a display of information for the operator on the display 54.

The input circuit 53 has a configuration similar to that of the input circuit 32 shown in FIG. 1. When the input device is manipulated by the operator, the input circuit 53 generates an input signal according to the manipulation and outputs the input signal to the control circuitry 51. The medical image processing apparatus 50 may include a touch panel having a configuration in which the input device is integrated with the display 54.

The display 54 has a configuration similar to that of the display 33 shown in FIG. 1. The display 54 displays 3D image data and the like generated by the control of the control circuitry 51 as a 3D image.

The communication control circuit 55 includes a connector using a combination of a parallel connection specification and a serial connection specification. The communication control circuit 55 has a function capable of performing a communication control according to the specifications and connecting to a network through a telephone line. With this configuration, the medical image processing apparatus 50 is connected to the network.

The 2D memory circuit 56 has a configuration similar to that of the 2D memory circuit 23 shown in FIG. 1. The 2D memory circuit 56 stores multiple 2D image data. The multiple 2D image data are transmitted through the communication control circuit 55, and positional data is attached to each piece of the multiple 2D image data.

The 3D memory circuit 57 has a configuration similar to that of the 3D memory circuit 28 shown in FIG. 1, and stores the volume data generated by the control circuitry 51.

Next, functions of the medical image processing apparatus 50 according to the present embodiment will be described.

Figure 15:
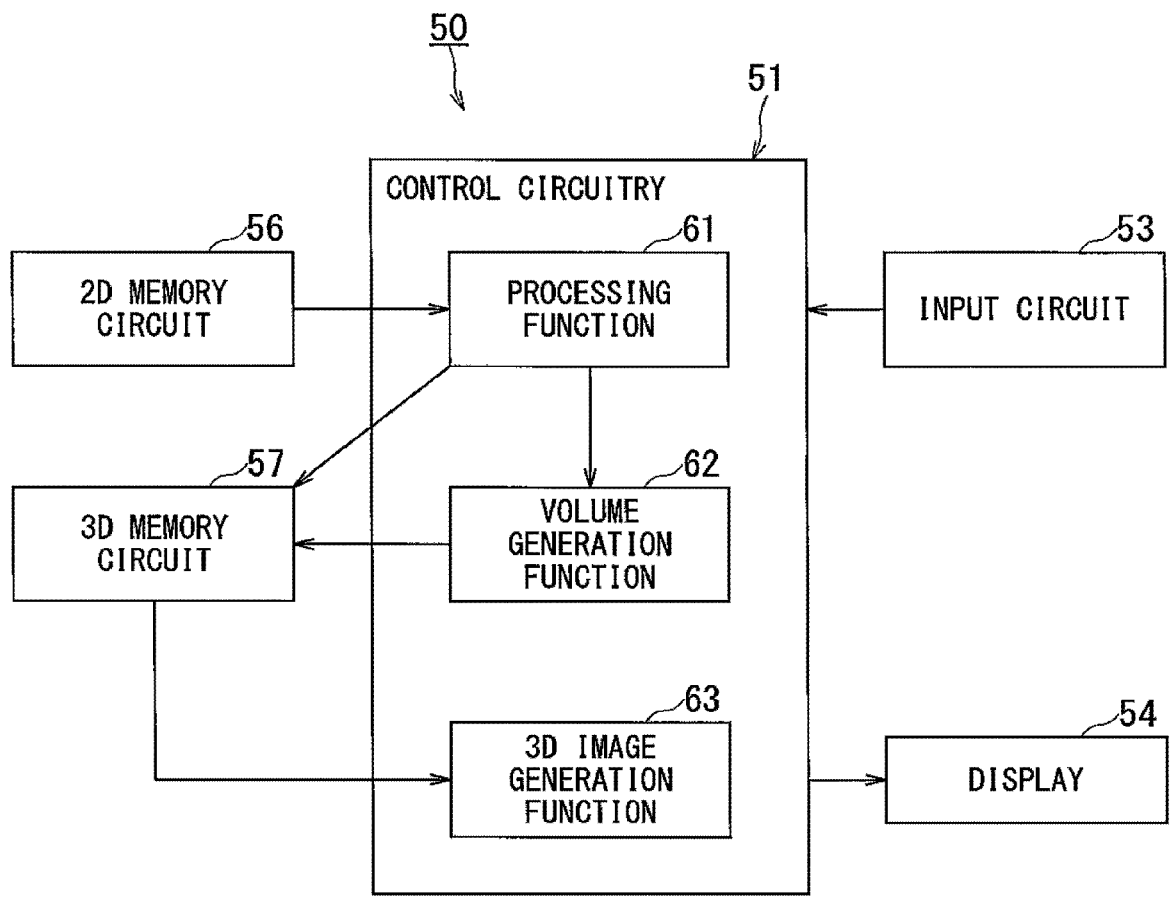
FIG. 15 is a block diagram showing functions of the medical image processing apparatus according to the present embodiment.

FIG. 15 is a block diagram showing functions of the medical image processing apparatus 50 according to the present embodiment.

The control circuitry 51 executes programs, and the medical image processing apparatus 50 functions as a processing function 61, a volume generation function 62, and a 3D image generation function 63. A case where the functions 61 to 63 function as software will be described by way of example. However, all or some of the functions 61 to 63 may be provided in the medical image processing apparatus 50 as hardware.

The processing function 61 has a function similar to the function performed by the processing circuit 26 shown in FIG. 1.

The volume generation function 62 has a function similar to the function performed by the volume generation circuit 27 shown in FIG. 1.

The 3D image generation function 65 has a function similar to the function performed by the 3D image generation circuit 29 shown in FIG. 1.

The medical image processing apparatus 50 performs processing in such a manner that the 2D image data set arranged in the 3D memory circuit 57 according to the positional data fits substantially inside the memory space of the 3D memory circuit 57, thereby making it possible to improve diagnostic capabilities using the 3D image to be displayed based on the 2D image data set. Further, the medical image processing apparatus 50 adjusts the orientation for the 2D image data set and then performs the reduction processing on the adjusted 2D image data set, while taking into consideration the spatial resolution, thereby making it possible to further improve diagnostic capabilities using the 3D image to be displayed based on the 2D image data set.

According to the ultrasonic diagnostic apparatus of at least one of the embodiments described above, it is possible to improve diagnostic capabilities using a 3D image to be displayed based on multiple 2D image data.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a transmitting and receiving circuit configured to transmit an ultrasonic wave to an ultrasonic probe and receive a signal based on the ultrasonic wave received by the ultrasonic probe;
a generation circuit configured to generate multiple frames of 2D image data in a chronological order based on the signal;
an acquisition circuit configured to acquire multiple positional data of the ultrasonic probe;
a memory circuit having a 3D memory space;
a processing circuit configured to:
relatively arrange the generated multiple frames of 2D image data according to the multiple positional data respectively, thereby unifying the arranged multiple frames of 2D image data to generate a unified multiple 2D image data set,
compare a size of the unified multiple 2D image data set with a size of the 3D memory space to determine whether the unified multiple 2D image data set fits inside the 3D memory space,
when the unified multiple 2D image data set does not fit inside the 3D memory space, perform processing on the unified multiple 2D image data set in such a manner that the unified multiple 2D image data set according to the multiple positional data fit inside the 3D memory space, thereby generate processed multiple 2D image data, and
store the processed multiple 2D image data into the 3D memory space, and
a volume generation circuit configured to generate volume data in the 3D memory space based on the stored processed multiple 2D image data after the processing, wherein
the processing circuit is configured to calculate an orientation for the unified multiple 2D image data set with respect to three orientations of the 3D memory space in such a manner that the unified multiple 2D image data set fits inside the 3D memory space, and perform orientation change processing on the unified multiple 2D image data set with respect to the orientation of the 3D memory space according to the calculated orientation.

2. The ultrasonic diagnostic apparatus according to claim 1, wherein the processing circuit is configured to:
determine multiple orientations for spaced frames of multiple 2D image data included in the multiple 2D image data set,
calculate multiple enlargement ratios when orientation change processing is performed on the unified multiple 2D image data set according to the determined multiple orientations, and
adopt a maximum value of the calculated multiple enlargement ratios as the enlargement ratio, perform orientation change processing on the unified multiple 2D image data set according to an orientation corresponding to the maximum value, and perform enlargement processing on the unified multiple 2D image data set at the enlargement ratio.

3. The ultrasonic diagnostic apparatus according to claim 1, wherein the processing circuit is configured to:
determine multiple orientations for spaced frames of multiple 2D image data included in the frames of multiple 2D image data,
calculate multiple reduction ratios when orientation change processing is performed on the unified multiple 2D image data set according to the determined multiple orientations, and
adopt a minimum value of the calculated multiple reduction ratios as the reduction ratio, perform orientation change processing on the unified multiple 2D image data set according to an orientation corresponding to the minimum value, and perform reduction processing on the unified multiple 2D image data set according to the reduction ratio.

4. The ultrasonic diagnostic apparatus according to claim 1, further comprising a 3D image generation circuit configured to generate 3D image data based on the volume data and display the 3D image data as a 3D image to a display.

5. The ultrasonic diagnostic apparatus according to claim 4, wherein the 3D image generation circuit is configured to display the generated 3D image to the display, while acquiring the multiple 2D image data.

6. The ultrasonic diagnostic apparatus according to claim 1, wherein the acquisition circuit is configured to acquire the multiple positional data from a sensor attached to the ultrasonic probe.

7. The ultrasonic diagnostic apparatus according to claim 1, wherein the processing circuit is configured to perform processing in such a manner that the entire unified multiple 2D image data set according to the multiple positional data fits inside the 3D memory space.

8. The ultrasonic diagnostic apparatus according to claim 1, wherein the processing circuit is configured to select predetermined frames of multiple 2D image data from the unified multiple 2D image data set, and perform processing in such a manner that the entire predetermined frames of multiple 2D image data arranged in the memory circuit according to the multiple positional data fit inside the 3D memory space.

9. The ultrasonic diagnostic apparatus according to claim 1, wherein the acquisition circuit is configured to acquire multiple 3D positional data corresponding to 3D positions of the ultrasonic probe.

10. The ultrasonic diagnostic apparatus according to claim 1, wherein the processing circuit is configured to perform processing comprising changing a frame pitch and number of frames of the unified data.

11. An ultrasonic diagnostic apparatus comprising:
a transmitting and receiving circuit configured to transmit an ultrasonic wave to an ultrasonic probe and receive a signal based on the ultrasonic wave received by the ultrasonic probe;
a generation circuit configured to generate multiple frames of 2D image data in a chronological order based on the signal;
an acquisition circuit configured to acquire multiple positional data of the ultrasonic probe;
a memory circuit having a 3D memory space;
a processing circuit configured to:
relatively arrange the generated multiple frames of 2D image data according to the multiple positional data respectively, thereby unifying the arranged multiple frames of 2D image data to generate a multiple 2D image data set,
compare a size of the unified multiple 2D image data set with a size of the 3D memory space to determine whether the unified multiple 2D image data set fits inside the 3D memory space,
when the unified multiple 2D image data set does not fit inside the 3D memory space, perform processing on the unified multiple 2D image data set in such a manner that the unified multiple 2D image data set according to the multiple positional data fits inside the 3D memory space, thereby generate processed multiple 2D image data, and
store the processed multiple 2D image data into the 3D memory space, and
a volume generation circuit configured to generate volume data in the 3D memory space based on the stored processed multiple 2D image data after the processing, wherein the processing circuit is configured to:
calculate an orientation for the unified multiple 2D image data and perform orientation change processing on the multiple 2D image data according to the unified orientation, and
calculate one of an enlargement ratio and a reduction ratio in such a manner that the unified multiple 2D image data set subjected to the orientation change processing fits inside the 3D memory space, and perform one of enlargement processing and reduction processing on the unified multiple 2D image data set subjected to the orientation change processing at the one of the calculated enlargement ratio and the calculated reduction ratio.

12. The ultrasonic diagnostic apparatus according to claim 11, wherein the processing circuit is configured to calculate an orientation for the unified multiple 2D image data set by matching an orientation for one frame of the multiple 2D image data among the multiple 2D image data with an orientation for the 3D memory space.

13. The ultrasonic diagnostic apparatus according to claim 12, wherein the processing circuit is configured to set 2D image data corresponding to a center frame selected from the multiple 2D image data frames as the one piece frame of the multiple 2D image data.

14. The ultrasonic diagnostic apparatus according to claim 11, wherein the processing circuit is configured to calculate an orientation for the unified multiple 2D image data set by matching an average orientation for orientations for multiple 2D image data frames selected from the multiple 2D image data set with an orientation for the 3D memory space.

15. A medical image processing apparatus for processing multiple 2D image data associated with multiple positional data, respectively, comprising:
a memory circuit having a 3D memory space; and
control circuitry configured to:
relatively arrange the multiple 2D image data according to the multiple positional data respectively, thereby unifying the arranged multiple 2D image data to generate a unified multiple i2D image data set,
compare a size of the unified 2D image data set with a size of the 3D memory space to determine whether the unified multiple 2D image data set fits inside the 3D memory space,
when the unified multiple 2D image data set does not fit inside the 3D memory space, perform processing on the unified multiple 2D image data set in such a manner that the unified multiple 2D image data set according to the multiple positional data fit inside the 3D memory space, thereby generate processed multiple 2D image data, store the processed multiple 2D image data into the 3D memory space, and generate volume data in the 3D memory space based on the stored processed multiple 2D image data after the processing, wherein the processing circuit is configured to calculate an orientation for the unified multiple 2D image data set with respect to three orientations of the 3D memory space in such a manner that the unified multiple 2D image data set fits inside the 3D memory space, and perform orientation change processing on the unified multiple 2D image data set with respect to the orientation of the 3D memory space according to the calculated orientation.

* * * * *